United States Patent [19]

Schmidt

[11] 4,070,248

[45] * Jan. 24, 1978

[54] DEVICE FOR MEASURING FRACTIONARY VOLUMES OF LIQUID SAMPLES

[75] Inventor: Jean-Michel Schmidt, Orgeval, France

[73] Assignee: Intertechnique, Plaisir, France

[*] Notice: The portion of the term of this patent subsequent to Oct. 19, 1993, has been disclaimed.

[21] Appl. No.: 713,487

[22] Filed: Aug. 11, 1976

Related U.S. Application Data

[63] Continuation-in-part of Ser. No. 582,764, June 2, 1975, Pat. No. 3,986,534.

[30] Foreign Application Priority Data

July 30, 1974 France .............................. 74.26426

[51] Int. Cl.² ........................... C12K 1/04; B65B 3/04
[52] U.S. Cl. ........................... 195/103.5 K; 195/139; 141/1; 141/34
[58] Field of Search .............. 195/103.5 R, 127, 139, 195/103.5 K; 141/1, 34, 57

[56] References Cited

U.S. PATENT DOCUMENTS 3,986,534   10/1976   Schmidt .............................. 195/139

Primary Examiner—Raymond N. Jones
Assistant Examiner—Robert J. Warden

[57] ABSTRACT

A device for measuring fractions of a liquid sample comprises a casing having a vertical axis and containing a central chamber and transparent cells distributed around the chamber and permanently vented to atmosphere. Each cell is connected to the chamber by a closure cup. A capillary constriction separates each pocket from the corresponding cell. The device may be used for the preparation of antibiograms.

11 Claims, 4 Drawing Figures

DEVICE FOR MEASURING FRACTIONARY VOLUMES OF LIQUID SAMPLES

CROSS REFERENCES TO RELATED PATENT APPLICATIONS

This application is a continuation-in-part of Pat. application Ser. No. 582,764 (U.S. Pat. No. 3,986,534).

BACKGROUND OF THE INVENTION

The present invention relates to devices for measuring predetermined volumes of a liquid sample and delivering such volumes to cells of the device where the volumes may be subjected to analytical operations.

Distributing devices are known in which a liquid sample in a storage vessel is distributed among a number of tubes. Such devices are for instance described in U.S. Pat. Nos. 3,766,016 and 3,770,027 (Guigan) and in U.S. Pat. No. 3,606,083 (Simon). However, they have drawbacks which are particularly serious when the device is used to distribute sample of infectious, noxious or dangerous liquids, e.g. preparations of micro-organisms. Considerable care should be exercised when handling the device and contamination may occur if the device is upset or handled carelessly while filled or operated.

SUMMARY OF THE INVENTION

An object of the invention is to provide a novel device for obtaining accurately metered fractions of predetermined volume of a liquid sample and for transferring them to test cells or tubes integral with the devices.

A further, more specific, object of the invention is to provide a device which is useful for testing susceptibility of bacteria contained in a liquid sample to different antibiotics and/or to different concentrations of antibiotics.

According to an aspect of the invention, there is provided a device for accurately measuring predetermined volumes of a liquid sample, comprising:

a casing having a central axis of rotation which is kept vertical in operation, a concentric upwardly open chamber to receive said liquid sample, a plurality of test cells having transparent side walls, distributed around said chamber and spaced radially therefrom, and a plurality of radial pockets each having an inner end communicating with said chamber and to be filled by liquid flowing from said chamber and an outer end communicating with a respective one of said cells by means defining a capillary constriction, and displaceable closure means arranged to separate said chamber from said pockets and to retain, in each of said pockets, the liquid volumes passed by gravity from said chamber to said pockets respectively, wherein a vent is formed in the wall of each said cell in the upper portion thereof.

The term "capillary constriction" is used to mean a passage which is of such size as to prevent the sample liquid from flowing therethrough when subjected to a hydrostatic pressure corresponding to a liquid head of a few centimeters. On the other hand, the constriction should have dimensions such that the sample liquid can be spun out into the cells when the liquid is subjected to an acceleration easy to obtain on a current centrifuge. The flow path of the liquid through the constriction should be such that the centrifugal acceleration, when the device is rotated, has a component which tends to drive the liquid out of the pockets. The flow path will typically be approximately radial with respect to the axis of the device.

Advantageously, each pocket is laterally bounded by vertical walls which are substantially parallel and radially directed and are at a distance not exceeding a few millimeters (1 to 5 mm in most cases). The top wall of each pocket can be flat, typically horizontal for easier manufacture. The lower wall is typically concave towards the top, over most of its extent at least.

The closure means may be cup-shaped. The side wall of the closure means may be shaped to cooperate with the lateral wall of the cylindrical central chamber. The contents of the pockets can be isolated from the chamber and from each other by forcing the edge of the cup wall against the lower wall of the chamber. The terminal edge of the side wall can be convex and can engage in a circular groove at the bottom of the chamber for sealing.

The invention has numerous applications, more particularly in medicine and biochemistry and, more generally, when the volumes have to be analysed using different reagents. The reagents, in dried or lyophilised form if necessary, can be placed beforehand in the cells. In the case, for example, where antibiograms by dilution in a liquid medium are to be obtained, the reagent may be a culture medium containing the antibiotic whose effect is to be measured, and an indicator, e.g. a pH indicator. A similar approach may be used for identifying strains of micro-organisms.

Since the cells have transparent walls, the analytical results can be determined visually or, more accurately, using a photocolorimeter or turbidity meter which can operate automatically. Opacity meters of known types can be used whenever a positive reaction is shown by a change in the transparency of the body of liquid in the cell. If the cells have parallel surfaces, each cell in turn may be conveyed between a suitable source of light and a suitable detector, which is disposed behind an optical filter if necessary.

The invention will be better understood from the following description of embodiments thereof, which are given by way of non-limitative examples.

DESCRIPTION OF PREFERRED EMBODIMENTS

Figure 1:
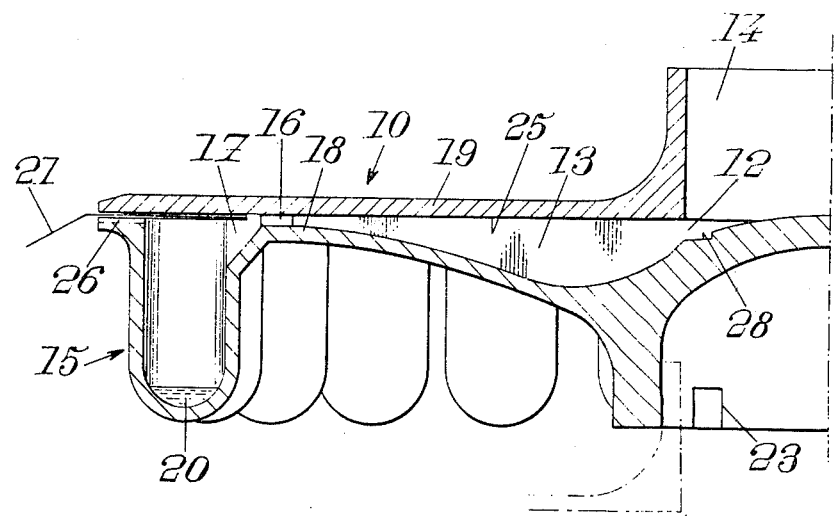
FIG. 1 is a simplified elevation view of an embodiment of the invention, partly in cross-section along a vertical plane, with the closure means removed.
Figure 2:
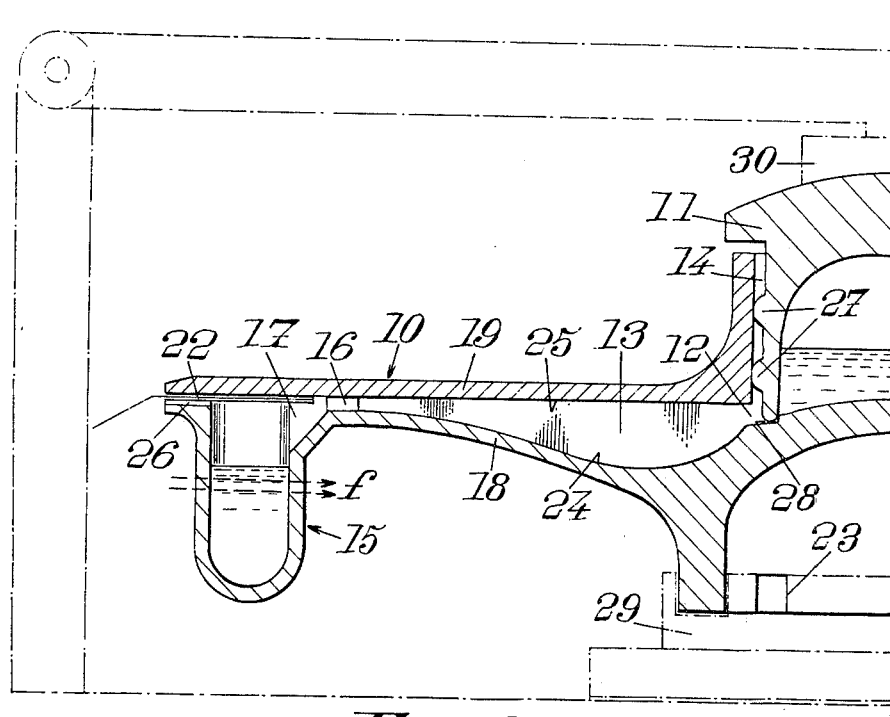
FIG. 2 shows the device of FIG. 1 after fractions of a sample have been transferred into analytical cells, the device being disposed on a centrifuge used for spinning the fractions into the cells of the pockets.

Referring to the drawings, FIGS. 1 and 2 show diagrammatic representation of a device for obtaining fractions of a liquid sample; the device comprises a casing 10, consisting of several assembled components, and removable closure means 11. The casing has a rotational symmetry around an axis which is located vertically during use. The casing contains a central chamber 14 which opens upwardly and has a capacity varying from a few millimeters to a few tens of milliliters. The chamber is connected via lateral apertures 12 to a number of pockets 13 formed in the casing, evenly distributed around the central chamber and extending substantially radially. Each pocket is associated with an analysis cell 15 in the form of a test-tube having a transparent side wall. A constriction 16 is provided between each pocket 13 and the corresponding cell 15, the transverse dimensions of each constriction being such that it is capillary for the liquid to be divided into fractions (the liquids can have greatly variable surface tensions). The connecting passage 17 provided between each constriction 16 and the corresponding cell 15 is flared so as to prevent the liquid in pockets 13 from seeping along the wall to cells 15.

The casing 10 in FIG. 1 comprises a bottom plate 18 and a top plate 19 force-fitted into one another. The bottom plate 18 forms the bottom of chamber 14, and the bottoms and side walls of pockets 13 and cells 15.

Since the side walls of the cells must be transparent, all of plate 18 is advantageously made of a plastics material which is transparent over a wide range of optical frequencies, which is rigid and which can be shaped by moulding. It can be made of crystal polystyrene, which withstands most conventional chemical reagents.

The top plate 19 forms the side wall of chamber 14, the top walls of pockets 19 and the covers of cells 15. It can be made of the same material as the bottom plate. The plates may be shaped so that the casings can be stored by stacking, as indicated by the chain-dotted lines in FIG. 1.

The casing shown in FIG. 1 contains a layer of reagent 20 at the bottom of each cell 15. In the case of a device for obtaining antibiograms, the reagent may be e.g. a culture medium containing a specific antibiotic and an indicator, e.g. a pH indicator.

A label 21 may be disposed opposite each cell so as to identify each antibiotic. In addition, an identification notch 23 can be formed in the lower skirt of plate 18 so that it can be mounted in only one angular position on a data-reading device.

A narrow slot 26 connects each cell to atmosphere, so that air can escape from it and the liquid can flow into it.

Advantageously, each pocket is flat in the vertical direction; to this end, the bottom plate has slits having vertical, parallel and approximately radial walls. The bottom 24 of each slot curves smoothly and is advantageously concave along its first part from the central chamber. The top wall 25 of the pockets may be flat and horizontal or slightly conical downwards or upwards, so as not to trap bubbles. In the illustrated casing, all pockets can have the same volume.

Typically, 36 pockets may be provided, each having a width of 1 mm or more; the constriction may have a minimum size of 0.1 mm. The diameter of the device may be something like 8 cm.

The device also comprises a closure member 11 (FIG. 2) which can be made of moulded material, e.g. the same material as plate 19. In the embodiment shown in FIG. 2, the side wall of the closure means 11 has beads 27 which are forced into the side wall of chamber 14, so that when the closure member has been completely pressed down it is retained in position. The terminal edge of the side wall of means 11 is rounded and bears against the bottom of a groove 28 formed at the bottom of the chamber so as to separate the interior thereof from pockets 13.

A way of operating the device according to the invention will now be described, when antibiograms are prepared.

A liquid sample is prepared, comprising a dilute solution of bacteria, the sensitivity of which is to be determined against various antibiotics in the device. The volume of sample need not be precisely determined, provided that it is sufficient to fill all the pockets. The sample is poured into the central chamber 14, from where it flows into the pockets, which it fills up to the constrictions 16. Next, the closure member 11 is positioned so as to separate the contents of pockets 13 (which form a corresponding number of pipettes) from the liquid remaining in chamber 14. When the closure means is in position, the dilute solution of bacteria cannot contaminate the environment.

Next, the device is placed on the rotating part of a centrifuge, which can be manual or driven by a motor at a given speed of rotation. FIG. 2 diagrammatically shows the device on top of the rotating part 29 of a centrifuge, the outline of which is shown by broken lines. The centrifuge frame has an arm bearing on closure member 11, the arm being sufficiently heavy to prevent the device from moving during centrifuging. A conventional centrifuge can be used. The electric motor is energized by a timing device so that the centrifuging conditions are reproducible.

After the contents of each pocket 13 has been transferred into the corresponding cell 15, the device is placed in an incubator. It is shaped so that it can easily be placed horizontally. After a sufficient period, usually about one day, the data are read, either visually or automatically.

The device can be used inter alia to prepare a wide variety of antibiograms from a small-volume sample. Different cells can contain different antibiotics, antibiotics at different concentrations, and/or different combinations of antibiotics. A plurality of devices can be provided and used in succession, a first device being used to determine the antibiotics towards which the strain is active or resistant, and a second device (whose cells contain different concentrations of the same antibiotics) being used to determine the minimum inhibiting concentration (CMI) of the active antibiotics.

Figure 3:
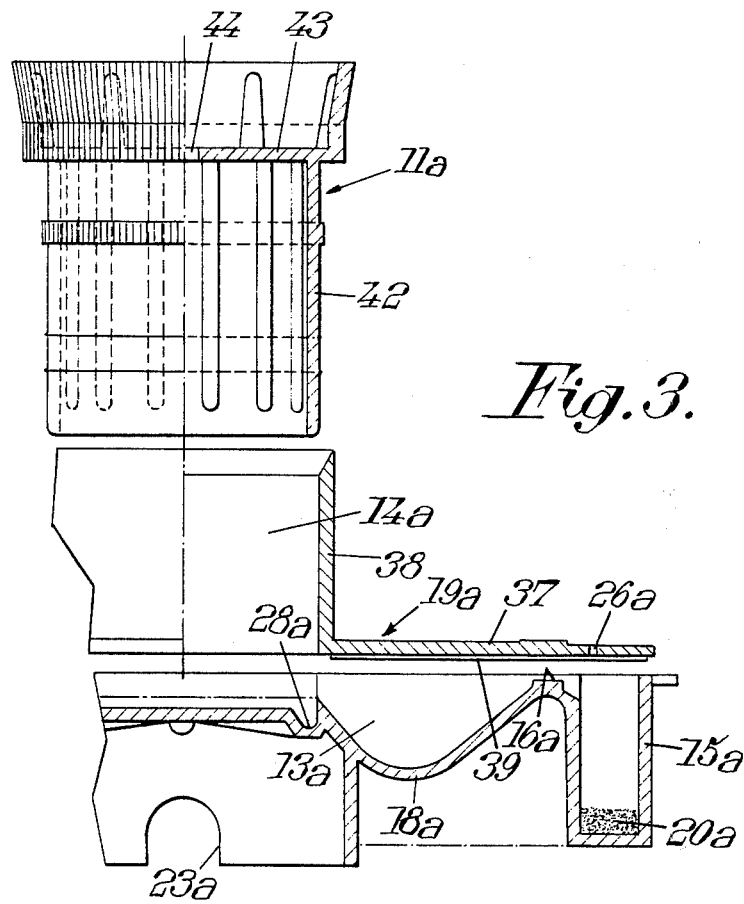
FIG. 3 is a view on an enlarged scale showing part of a device according to a modified embodiment, in vertical cross-section, before assembly.
Figure 4:
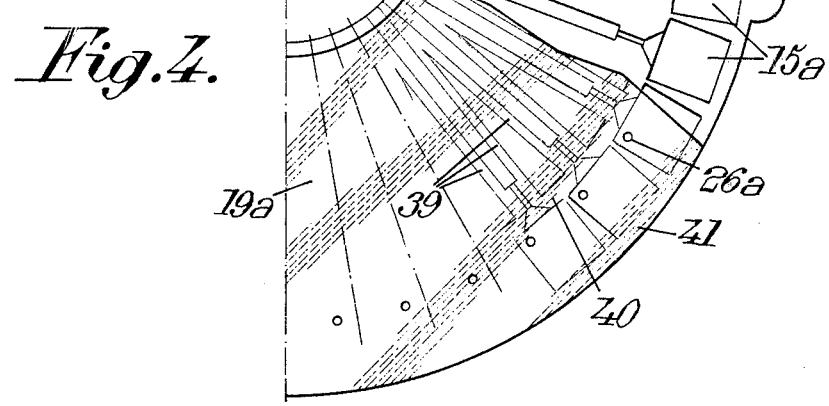
FIG. 4 is a plan view of a fraction of the device shown in FIG. 3, partly with the upper portion of the casing removed.

FIGS. 3 and 4 (where, for simplicity, those elements which have a counterpart in FIG. 1 are designated by the same reference numeral with a *a* mark affixed thereto) show a modified embodiment, designed for achieving a high degree of accuracy in the measurement of the liquid samples which are dispensed to the cells.

For that purpose, the embodiment of FIGS. 3 and 4 is provided with constrictions of small cross-sectional area for preventing minute amounts of liquid to be forced into some cells when liquid is spilled into the central chamber. The cup-shaped closure member is so designed that it does not exert any piston type effect tending to force liquid out of the chamber into those cells which are provided with the constructions of larger cross-sectional area (some amount of dispersion being unavoidable due to manufacturing tolerances). Decreasing the cross-section of the constrictions results in a requirement for higher rotational speed for forcing the liquid into the cells. An appropriate location of the vent in each cell is selected for preventing liquid drops from being spun out of the cells into atmosphere when centrifuging the device.

Again, the device illustrated in FIGS. 3 and 4 consists of a casing 10*a* and a removable cup-shaped closure member 11a. The casing is manufactured from a bottom part 18a and a top plate 19a, both of which may be made of polystyrene by castings. The bottom part 18a comprises 36 cells 15a distributed at 10° intervals about the axis of the part, without any gap between the walls of adjacent cells. As shown in FIG. 4, the cells have a square horizontal cross-section. They are typically 5 mm wide if the device has an overall diameter of 8 cm or so. The bottom part 18a also constitutes the lower walls and side walls of 36 pockets 13a, typically about 1 mm wide, each communicating with a respective cell via a constriction 16a, typically 0.2 mm wide and 0.2 mm deep.

The central portion of the bottom part 18a constitutes the lower wall of the central chamber 14a. At the periphery of that portion, there is formed an annular slot 28a adapted to receive the terminal edge of the closure member 11a. The radially inwardly facing surface of that slot is substantially cylindrical while the outwardly facing surface is generally frustoconical.

The top plate 19a has a flat annular outer portion 37 and a cylindrical tubular portion 38 adapted to receive and frictionally retain the cup-shaped closure member 11a. The opening portion of the internal surface of portion 37 has a flared shape which renders insertion of the closure member 11a easier.

Before it is secured to the bottom part 18a the underside of the flat outer portion 37 of plate 19a is formed with two sets of ridges which protrude slightly from the plate and typically have a triangular cross-section with a height of 0.2–0.3 mm. The ridges are for easier connection of parts 18a and 19a using ultrasonic welding. The ridges concentrate ultrasonic energy, whereby welding of the top plate 19a and bottom part 18a is made along accurately determined lines. The ridges 39 of a first set are radially directed and located at 10° intervals. They separate the pockets and cells from each other. Another set of ridges comprises two circumferential concentric ridges 40 and 41 which achieve closure of the cells.

As indicated above, parts 18a and 19a are secured to each other by ultrasonic welding. The bottom part 18a is located on a support. The top plate is located on the bottom part in a proper angular position. A sonotrode is located on the top plate and presses it onto the bottom part. Ultrasonic energy is applied and concentrates in the ridges integral with the top plate, thereby achieving welding. For more clarity, an outline of the sonotrode is indicated by dash-dot circles on FIG. 4.

Due to the small flow cross-sectional area of the constrictions 16a, the device should be rotated at high speed for projecting the liquid volumes from the pockets 13a into the cells 15a. If vents were located in radial alignment with the constrictions, there would be a substantial risk of leakage or spillage of liquid. In the embodiment of FIGS. 3 and 4, that difficulty is overcome by locating a vent in the form of a hole 26a formed in the top plate 19a in a radially inner corner of each cell 15a. The hole is preferably in the leading corner of each cell in the direction of rotation of the centrifuge. A circular vent hole 1 mm in diameter provides satisfactory result in a device having the size referred to above.

Closure member 11a (FIG. 3) has a cylindrical side wall 42 and an end wall 43 formed with a central venting aperture 44 intended to prevent air pressure build-up in the central chamber 14a when the closure member is inserted. The venting aperture will typically be 2-4 mm in diameter.

The outer surface of the lateral wall 42 is substantially cylindrical for preventing fluid from being forced into cells during the final insertion travel of the closure member. That arrangement is to be compared with that of FIG. 2, in which the pockets remain in communication even when the closure member is fully inserted and consequently there may be some minute amount of liquid forced through the larger ones of the restrictions, thereby detrimentally affecting the accuracy of metering. However, a sealing action is provided by two ridges 45 integral with the closure member and protruding by a minute amount (for instance 0.1 mm). In the upper portion of the lateral wall 42, there is provided a knurled peripheral portion 46 for frictionally retaining the closure member after it has been inserted. The lateral wall may be formed with longitudinal reinforcements 47.

Operation of the device is quite similar to that of the device illustrated in FIGS. 1 and 2: after a sample of sufficient volume for filling the pockets 13a has been spilled into chamber 14a, the closure member 11a is fully inserted. As soon as the lower edge of closure member 11a has travelled beyond the peripheral edge 46 formed on the lower part 18a, the pockets are separated from each other and from chamber 14a. During the final travel of the closure member, the lower portion thereof is forced radially outwardly by the internal wall of slot 28a, thereby improving fluid tightness. Then the device is put on a centrifuge which projects the predetermined volumes of liquid in the pockets 13a into the respective cells 15a.

The device of FIGS. 3 and 4 is of particular interest for preparing antibiograms, since it makes it possible to obtain a large number of liquid samples having the same volume which may be associated with different antibiotics.

In a particular embodiment which has proved satisfactory the thirty-six cells are distributed as follows:

the first two cells (Nos. 1 and 2) are reserved for reference and do not locate any solid product, the next two cells (Nos. 3 and 4) receive a bacteria growing medium without any growth inhibiting material, the next thirty-two cells are for testing the susceptibility of those bacteria which may be present in the liquid sample to different antibiotics. Preferably, each antibiotic is present in two different cells at different concentrations, one of which is the normal concentration in the human body which is used for therapeutic purpose, the other of which is the maximum concentration which is acceptable and depends on the toxicity or side effects of the antibiotic agent. Typically, cell No. 5 will contain a first antibiotic at the normal concentration $c$ and cell No. 6 the same antibiotic with the maximum tolerable concentration $C$ and so on.

If the device is for determining infections of the urinary tract, the antibiotics may be as follows:

Nos. 5 and 6 : sulfamethoxazol trimetoprime (concentrations: 2 and 16 $\mu$g/ml)

Nos. 7 – 8 : nalidixic acid (concentrations: 8 and 32 $\mu$g/ml).

Nos. 9 – 10 : oxolinic acid (concentrations: 8 and 32 $\mu$g/ml).

Other antibiotics which may be tested simultaneously are colistine, polymyxine B, chloramphenicol, doxycycline, minocycline, streptomycine, kanamycine, lividomycine, tobramycine, gentamycine, carbenicilline, cefaloridine, ampicilline, etc. The concentrations to be used will of course depend on the nature of the antibiotic.

After incubation, reading may be as follows.

The device is located on a rotary part of a reading system. A step by step advance mechanism is provided for locating each cell in turn, beginning with cell No. 1, between a light source and a light detector. The light detector is connected to an electronic system comprising a threshold detector having an adjustable threshold.

A sequential mechanism of the reading system initiates a sequence of operations which may be as follows.

First, cell No. 1 is located between the light source and the light detector. Light attenuation is by the transparent walls only and the resultant signal is stored as a reference in analog or digital form.

Cell No. 2 is moved and a new measurement is made. Under normal operating conditions, the signal received by the light detector will be the same as during the first measurement. Any discrepancy may indicate a disturbance in the measuring system or a deterioration of the device. If there is no discrepancy, then the second signal is stored. Based on the average of the two signals, the measuring system then determines a threshold which will correspond to the maximum amount of light which will be received by the light detector through a cell in which unrestricted growth of bacteria has taken place.

That amount of light will of course correspond to a predetermined fraction of the light which was transmitted through cells 1 and 2.

Then the same measurements are made on cells 3 and 4. Since there is no antibiotic in either cell, then bacteria should have grown freely in the culture medium and the light detector should receive an amount of light lower than the threshold. The threshold detector then will deliver a signal which will be referred to in the following as "+". If a "+" signal is not delivered, this is an indication that operation of the device is not correct or there is no bacteria.

Cell No. 5, containing a first antibiotic at a normal concentration, is then moved between the source and detector. If growth has not been inhibited by that concentration, then a "+" signal will be delivered. If inhibition has taken place and the liquid volume has remained limpid and light transmitting, then a "−" signal will be delivered, indicating that the bacteria is sensitive to the antibiotic.

Cell No. 6, containing the same antibiotic as cell No. 5, at maximum concentration, is then moved to a location between the source and detector and the same measurement is repeated. If bacteria growth has been inhibited by the normal concentration, then a "−" signal will be delivered; a "+" signal would indicate missoperation or some failure. Assuming a "+" signal was obtained during the measurement on cell No. 5, then either a "+" signal (indicating that the bacteria is resistant to the antibiotic) or a "−" signal (indicating that the bacteria strain present in the sample has a susceptibility to the antibiotic which may be considered as intermediate) may be obtained.

The same sequence is repeated on all thirty-six cells. Finally, a table somewhat as follows may be obtained, which may be prepared by an operator or automatically typed by the system if operated automatically.

| Nos. | Reading | | Antibiotic | Concentration (μg/ml) | |
|------|---------|---|------------|---|---|
|      |         |   |            | c | C |
| 3-4  | +       | + |   | none |   |   |
| 5-6  | +       | + | R | sulfamethoxazol trimethoprime | 2 | 16 |
| 7-8  | −       | − | S | nalidixic acid | 8 | 32 |
| 9-10 | +       | − | I | oxolinic acid | 8 | 32 |
| 11-12| +       | + | R | colistine | 2 | 16 |
| etc. |         |   |   |   |   |   |

Rather than containing antibiotics, some of the cells may contain reagents for detecting the presence of components in biologic samples, for instance urea or desaminase. Then, an identification reagent should be provided and measurement with respect to such cells will preferably be made by colorimetry.

Many other modified embodiments of expendable devices according to the invention are possible. When used for medical purpose, the device is used once only and then destroyed.

I claim:

1. A device for accurately measuring predetermined volumes of a liquid sample, comprising:
   a casing having a central axis of rotation which is kept vertical in operation, a concentric upwardly open chamber to receive said liquid sample, a plurality of test cells having transparent side walls, distributed around said chamber and spaced radially therefrom, and a plurality of radial pockets each having an inner end communicating with said chamber and to be filled by liquid flowing from said chamber and an outer end communicating with a respective one of said cells by means defining a capillary constriction,
   and displaceable closure means arranged to separate said chamber from said pockets and to retain, in each of said pockets, the liquid volumes passed by gravity from said chamber to said pockets respectively,
   wherein a vent is formed in the wall of each said cell in the upper portion thereof.

2. A dispensable device for testing antibiotic susceptibility of bacteria in a liquid sample, comprising:
   a casing having a vertical axis,
   an annular wall in said casing defining an upwardly open central chamber,
   a plurality of radially directed pockets formed in said casing communicating with said chamber via openings in said annular wall and angularly distributed about said chamber,
   a plurality of transparent test cells arranged in a circular row around said pockets, each provided with a venting opening in the upper portion thereof,
   means defining a capillary liquid flow constriction, connecting each said test cell to a respective one of said pockets,
   closure means arranged to substantially sealingly engage said lateral wall of said chamber and to close said openings, thereby separating said cells from said chamber,
   said cells containing a bacteria culture medium and at least some of said cells containing an antibiotic at a predetermined concentration.

3. A device according to claim 2, wherein each said pocket has lateral vertical walls which are substantially parallel and radial with respect to the axis, and an upper wall which is substantially flat and a lower wall which is upwardly concave, at least over most of its extent.

4. A device according to claim 2, wherein the closure means comprises a cylindrical side wall adapted to be inserted into the chamber to separate said pockets from each other and from the chamber, and an apertured upper end wall.

5. A device according to claim 4, wherein the side wall of the closure means and the chamber are so shaped and proportioned that the closure means is retained in the chamber when manually positioned therein.

6. A device according to claim 4, wherein the side wall of the closure means has a terminal edge arranged to engage into a peripheral slot formed in the casing to separate the chamber from the pockets.

7. A device according to claim 2, wherein the casing comprises:
 a lower part of transparent rigid material forming said cells, said vertical side walls and lower wall of the pockets and a bottom wall of said chamber,
 and an upper part made of plastic material having a substantially flat portion, covering the bottom plate, and ultrasonically welded to said bottom plates along ridges protruding from the surface of said upper part confronting said lower part.

8. A device according to claim 7, wherein the venting opening of each said cell is formed through the upper part out of radial alignment with the constriction associated with the cell.

9. A device according to claim 8, wherein each cell is of substantially square cross-section and the venting opening is formed in a radially inner corner thereof.

10. A device according to claim 2, wherein the device comprises two reference cells devoid of bacteria growth inhibiting material and a plurality of cells associated by pairs, one cell of each pair comprising a predetermined antibiotic at a normal therapeutic concentration and the other cell of said pair containing the same antibiotic at a maximum tolerable concentration.

11. A method for testing susceptibility of bacteria in a liquid sample to a plurality of different antibiotics, comprising the steps of:
 providing a rotatable casing defining an upwardly open central chamber concentric with the rotational axis of said casing, a plurality of radial pockets communicating at the inner ends thereof with said central chamber for gravity flow of liquid from said chamber into each of said pockets, the outer ends of each of said pockets communicating by means of a flow restriction with each of the plurality of vented test cells formed in the rotatable casing, some at least of said cells containing a bacteria growing medium and an antibiotic in lyophylised form,
 filling said central chamber with said liquid sample until the pockets are filled up to said constrictions by gravity flow from said chamber,
 inserting said closure means to isolate said predetermined volumes of liquid in said pockets,
 rotating said casing about said axis to create centrifugal forces sufficient to overcome said capillary forces and to cause transfer of said volumes from said pockets into said test tubes,
 incubating said bacteria for a predetermined time period, and optically determining the growth of bacteria in each said cell.

* * * * *